United States Patent
Krasnow (10) Patent No.: US 10,413,676 B1
(45) Date of Patent: Sep. 17, 2019

(54) ULTRASOUND TRACKING OF MEDICATION DELIVERY BY MEDICATION INJECTION DEVICES

(71) Applicant: Verily Life Sciences LLC, Mountain View, CA (US)

(72) Inventor: Benjamin David Krasnow, Redwood City, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 94 days.

(21) Appl. No.: 15/790,932

(22) Filed: Oct. 23, 2017

Related U.S. Application Data (60) Provisional application No. 62/411,926, filed on Oct. 24, 2016.

(51) Int. Cl.
*A61M 5/315* (2006.01)
*A61B 5/00* (2006.01)
*A61M 5/142* (2006.01)

(52) U.S. Cl.
CPC ....... *A61M 5/31568* (2013.01); *A61B 5/0026* (2013.01); *A61B 5/4839* (2013.01); *A61B 5/4848* (2013.01); *A61M 5/142* (2013.01); *A61B 5/002* (2013.01); *A61M 2205/33* (2013.01)

(58) Field of Classification Search
CPC ............ A61M 5/1684; A61M 5/31511; A61M 5/31513; A61M 5/31521; A61M 5/3156; A61M 2205/3375; A61M 2205/3379; A61M 2205/3389; A61M 2205/70; G01F 1/7082; G01F 11/027; G01F 23/296–2968
See application file for complete search history.

(56) References Cited

U.S. PATENT DOCUMENTS

| | | | |
|---|---|---|---|
| 5,311,871 A | 5/1994 | Yock | |
| 5,728,074 A | 3/1998 | Castellano et al. | |
| 6,113,578 A * | 9/2000 | Brown | A61B 5/14532 604/207 |
| 6,270,455 B1 * | 8/2001 | Brown | G06F 19/3468 600/300 |
| 6,819,629 B2 | 11/2004 | Cummings et al. | |
| 2001/0034506 A1 * | 10/2001 | Hirschman | A61M 5/14546 604/207 |
| 2005/0049505 A1 | 3/2005 | Wu et al. | |
| 2007/0244469 A1 * | 10/2007 | Ozeri | A61K 9/0009 604/891.1 |

(Continued)

*Primary Examiner* — Kami A Bosworth
(74) *Attorney, Agent, or Firm* — Christensen O'Connor Johnson Kindness PLLC (57) ABSTRACT

A medication injection device includes a plunger head having an elastomer housing that fits within a barrel. The plunger head includes an ultrasonic transducer that sends and receives ultrasonic signals in the form of ultrasonic waves, an antenna, a microcontroller that interfaces with the ultrasonic transducer and the antenna, and a power source that powers the microcontroller and the ultrasonic transducer. The ultrasonic transducer, the antenna, the microcontroller, and the power source may be at least partially encapsulated in the elastomer housing. The microcontroller may be programmed to measure echo times of the ultrasonic waves, compare consecutive echo times, and apply a compensation factor. The microcontroller may also be programmed to calculate a volume of medication dispensed from the barrel.

10 Claims, 5 Drawing Sheets

(56) References Cited

U.S. PATENT DOCUMENTS

| | | | |
|---|---|---|---|
| 2009/0043253 A1 | 2/2009 | Podaima | |
| 2010/0286612 A1 | 11/2010 | Cirillo et al. | |
| 2010/0288036 A1* | 11/2010 | Volkwein | G01B 17/00 73/114.29 |
| 2012/0065588 A1 | 3/2012 | Cirillo et al. | |
| 2013/0310756 A1* | 11/2013 | Whalley | A61M 5/31 604/189 |
| 2014/0207080 A1* | 7/2014 | Allerdings | A61M 5/24 604/207 |
| 2014/0249410 A1* | 9/2014 | Uber, III | A61M 5/31573 600/432 |
| 2014/0296787 A1* | 10/2014 | Agard | A61M 5/14216 604/152 |
| 2015/0112316 A1 | 4/2015 | Cudak et al. | |
| 2015/0174330 A1* | 6/2015 | Nagel | A61M 5/315 604/218 |
| 2015/0174342 A1 | 6/2015 | Mitrosky et al. | |
| 2015/0209510 A1 | 7/2015 | Burkholz et al. | |
| 2017/0136185 A1* | 5/2017 | Rios | A61M 5/31511 |
| 2017/0189625 A1 | 6/2017 | Cirillo et al. | |
| 2018/0200451 A1* | 7/2018 | Shekalim | A61M 5/31525 |

* cited by examiner

ULTRASOUND TRACKING OF MEDICATION DELIVERY BY MEDICATION INJECTION DEVICES

REFERENCE TO RELATED APPLICATIONS

This application claims priority to U.S. Provisional Patent Application Ser. No. 62/411,926 filed Oct. 24, 2016. U.S. Provisional Patent Application Ser. No. 62/411,926 is hereby incorporated by reference.

TECHNICAL FIELD

The present disclosure relates generally to the field of tracking of medication delivery using medication injection device, and more particularly, apparatuses and methods of improved ultrasound tracking of medication delivery by medication injection devices.

BACKGROUND DESCRIPTION

Measuring the quantity and recording the timing of a drug's administration is an integral part of many disease treatments. For many treatments, to achieve the best therapeutic effect, specific quantities of a drug may need to be injected specific times of day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range. Currently, there are a limited number of methods or devices for automatically tracking the drug administration without requiring the user to manually measure and record the volume, date, and time. A variety of glucose injection syringes/pens have been developed, but there is much room for significant advancement in the technology in order to reduce the size, lower the cost, and enhance its functionality, accuracy, and reliability thus making it a more viable long-term solution. For example, current insulin pens are often disposable, but do not include dosage tracking. A smaller portion of the market is composed of reusable pens which are more expensive, and still do not include good dosage-tracking capabilities.

SUMMARY

The present disclosure is directed to systems and methods of drug administration using a syringe with a smart plunger head.

In one aspect, the present disclosure is directed to a plunger head for a medication injection device. The plunger head may include an elastomer housing that fits within a barrel of the medication injection device. The plunger head may also include an ultrasonic transducer that sends and receives ultrasonic signals in the form of ultrasonic waves, an antenna, a microcontroller that interfaces with the ultrasonic transducer and the antenna, and a power source that powers the microcontroller and the ultrasonic transducer. The ultrasonic transducer, the antenna, the microcontroller, and the power source may be at least partially encapsulated in the elastomer housing. The microcontroller may be programmed with instructions to measure echo times of the ultrasonic waves and compare consecutive echo times and if a change in distance corresponding to a change in the consecutive echo times is indicative of an error, the microcontroller may apply a compensation factor to the change in distance. The microcontroller may also be programmed with instructions to calculate a volume of medication dispensed from the barrel based on the change in distance of the plunger head.

In another aspect, the present disclosure is directed to a method of tracking administering of a medication delivered by a medication injection device. The method may include depressing a plunger of the medication injection device and sending and receiving ultrasonic signals in the form of ultrasonic waves from a plunger head installed within a barrel of the syringe. The method may also include measuring the echo times of the ultrasonic waves, wherein the echo time is the time it takes for an ultrasonic wave to travel through the medication to an end of a barrel, reflect, and return to the plunger head. The method may further include comparing consecutive echo times and if a change in distance corresponding to a change in the consecutive echo times is indicative of an error, the microcontroller applies a compensation factor to the change in distance. The method may also include calculating a volume of the medication dispensed based on a distance the plunger head travels.

DETAILED DESCRIPTION

Reference will now be made in detail to embodiments of the present disclosure, examples of which are illustrated in the accompanying drawings. Where possible, the same reference numbers will be used throughout the drawings to refer to the same or like parts.

Figure 1:
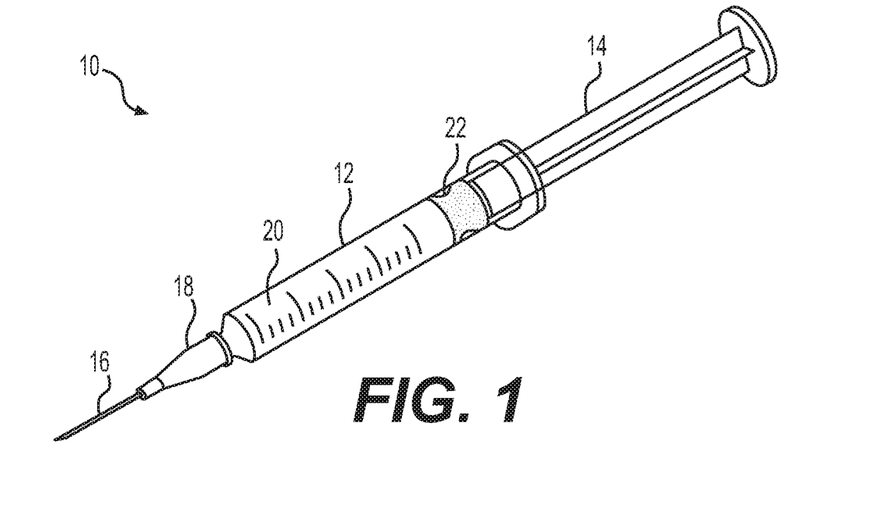
FIG. 1 is a perspective view of a medication injection device, which includes a plunger head according to an exemplary embodiment.

FIG. 1 shows a perspective view of a medication injection device 10 designed for ejecting a fluid. Medication injection device 10 may include a barrel 12, a plunger 14, a needle 16, and a hub 18 connecting needle 16 to barrel 12. Barrel 12 may be configured to contain a fluid, for example, a medication 20 and medication injection device 10 may be configured to dispense medication 20 from needle 16 when plunger 14 is depressed. A standard medication injection device (e.g., a syringe) usually contains a plunger head at the end of the plunger that seals off the open top of the barrel and forces the fluid out the needle when the plunger is depressed. The plunger head for a standard medication injection device is usually a unitary piece of molded plastic or rubber.

For medication injection device 10 shown in FIG. 1, the standard plunger head has been replaced with a smart or intelligent plunger head 22 that is configured to measure and register the quantity of medication 20 administered and the date and time of administration. Plunger head 22 may be installed in a standard medication injection device by withdrawing plunger 14 and removing the standard plunger head and installing smart plunger head 22. In some embodiments, medication injection device 10 may be manufactured and supplied with a smart plunger head 22 preinstalled. Smart plunger head 22 may be referred herein as either smart plunger head 22 or plunger head 22.

Plunger head 22 may be sized to correspond with the size of barrel 12. For example, plunger head 22 may be formed to fit any size medication injection device 10. For example, plunger head 22 may be sized to fit a 1 ml, 2 ml, 3 ml, 5 ml, 10 ml, 20 ml, 30 ml, or 50 ml medication injection device.

Figure 2:
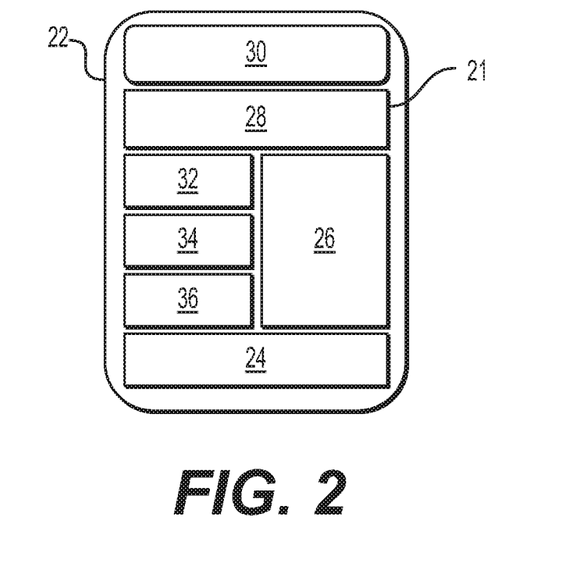
FIG. 2 is a schematic of the plunger head of FIG. 1.

FIG. 2 shows a schematic of plunger head 22, according to an exemplary embodiment. Plunger head 22 may include an ultrasonic transducer 24, a microcontroller 26, a power source 28, and an antenna 30 (e.g., for near field communication (NFC), which in some embodiments may be a transceiver (e.g., for BLUETOOTH low energy (BLE) communication). In some embodiments, the components of plunger head 22 may be at least partially encapsulated in an elastomer (e.g., rubber, ethylene propylene (EPM), nitrile rubber (NBR), ethylene propylene diene (EPDM), polybutadiene, and polyisoprene). Ultrasonic transducer 24 may be configured to send and receive ultrasonic signals. Microcontroller 26 may be programmed with instructions to control the overall operation of the plunger head. Antenna 30 may be configured to wirelessly communication with a remote device (e.g., a smart phone, a glucose monitor, an insulin pump, and a computer) using one or more wireless communication methods. The one or more wireless communication methods may include, for example, radio data transmission, Bluetooth, BLE, NFC, infrared data transmission, electromagnetic induction transmission, and/or other suitable electromagnetic, acoustic, or optical transmission methods. Power source 28 may be configured to power ultrasonic transducer 24, microcontroller 26, and Antenna 30.

Microcontroller 26 may include one or more processors, including for example, a central processing unit (CPU). The processors may include any suitable type of commercially available processor or may be a custom design. Microcontroller 26 may include additional components, for example, non-volatile memory (e.g., a flash memory), volatile memory (e.g., a random access memory (RAM)), and other like components, configured to store information and/or programmed instructions).

In some embodiments, plunger head 22 may also include a crystal oscillator 32 configured to keep accurate time so that the date and time of each injection may be accurately recorded and stored in memory of microcontroller 26. Crystal oscillator may be, for example, a 32 KHZ crystal oscillator. In some embodiments, crystal oscillator 32 may be internal to microcontroller 26. In some embodiments, an external high speed RC oscillator (e.g., 10 MHZ) may be used to provide sufficient time accuracy to measure the echo times.

Power source 28 may be any suitable power source. For example, power source 28 may be a battery, a capacitor, or the like. In some embodiments, power source 28 may be rechargeable via wireless energy transmission, for example, inductive coupling, resonant inductive coupling, radio frequency (RF) link, or the like. In some embodiments, power source 28 may be a non-rechargeable battery that is configured to last the operational life of plunger head 22, for which the operational life may be about 1 year, about 2 years, about 3 years, or more. For example, in some embodiments, power source 28 may be a watch battery. In some embodiments, where plunger head 22 is a passive device as described herein, power source 28 may be eliminated.

Antenna 30 may be used to communicate with a variety of remote devices (e.g., smart phones, glucose monitors, insulin pumps, computers, etc.). Plunger head 22 may transmit the information via any suitable wireless communication method. For example, in some embodiments, plunger head 22 may utilize radio data transmission, BLUETOOTH or BLE, NFC, infrared data transmission or other suitable method. In some embodiments, information may also be wirelessly transmitted from a remote device to plunger head 22 via antenna 30. For example, the date and time may be set by writing to microcontroller 26 via the wireless communication.

As shown in FIG. 2, in some embodiments, plunger head 22 may also include force sensor 34. Force sensor 34 may be configured to detect when a force is applied to plunger head 22 via plunger 14, which for example may indicate that dispensing of medication is being initiated. Force sensor 34 may be, for example, a simple spring-loaded switch that is molded into the plunger head 22. In some embodiments, ultrasonic transducer 24 may be configured to function as a force sensor thereby eliminating the need for a separate force sensor 34. For example, ultrasonic transducer 24 may have a piezoelectric element that may detect the dynamic changes in pressure when a user depresses the plunger 14.

In some embodiments, as shown in FIG. 2, plunger head 22 may include a temperature sensor 36. Temperature sensor 36 may be configured to measure the temperature of medication 20. Microcontroller 26 may be configured to use the temperature of medication 20 to compensate for variations in the temperature that would affect the speed of sound within the medication, thus improving the accuracy of the distance and volume calculations. In some embodiments, microcontroller 26 may also use temperature sensor 36 to monitor the temperature of medication 20 to ensure that the temperature of medication 20 stays within an acceptable range. The efficacy of some medications is affected by temperature.

Figure 3:
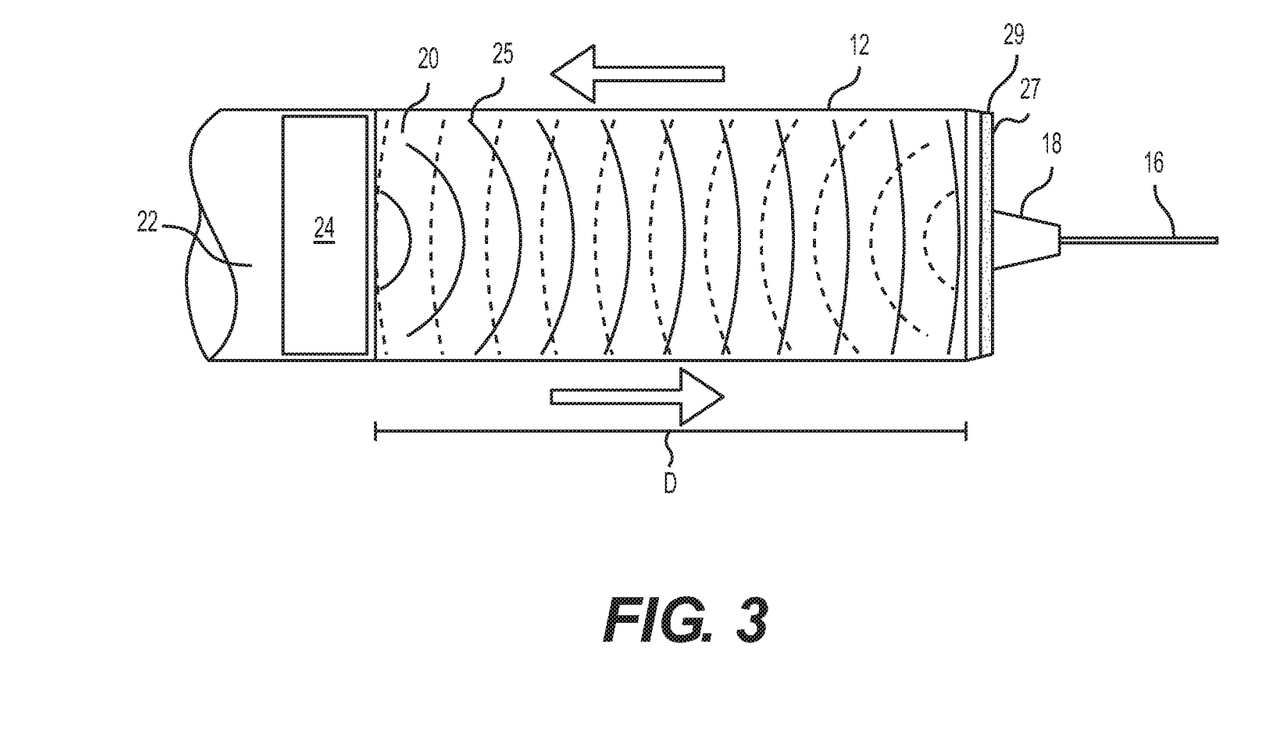
FIG. 3 is a schematic illustrating the behavior of ultrasonic signals transmitted by the plunger head of FIG. 2.

Ultrasonic transducer 24 may be an actuator, piezoelectric element, or speaker-like voice coil configured to generate and send a pressure wave or ultrasonic signals in the form of ultrasonic waves. In some embodiments, ultrasonic transducer may be a resonant thickness-mode transducer. Ultrasonic transducer 24 may be sized to be slightly smaller than the inner diameter of barrel 12. As shown in FIG. 3, ultrasonic transducer 24 may be configured to generate ultrasonic signals 25 (e.g., radiated ultrasonic sound energy waves) and send the ultrasonic signals 25 down barrel 12 toward hub 18 and needle 16. The frequency of the ultrasonic signals 25 may be determined by the thickness of ultrasonic transducer 24. By vary the thickness of ultrasonic transducer 24 the frequency of the ultrasonic signals 25 may be varied. For example, the frequency range for the ultrasonic signals may range from about 2 MHz to about 4 MHz, about 2 MHz to about 3 MHz, or about 3 MHz to about 4 MHz. In some embodiments, the static capacitance of the ultrasonic transducer 24 may also be varied. For example, in some embodiments the static capacitance may be about 900 pF, about 800 pF, about 700 pF, or less. According to one illustrative embodiment, for an ultrasonic transducer 24 having a static capacitance of about 900 pF, one ultrasonic pulse of the ultrasonic signals 25 may be generated by supplying about 3V to ultrasonic transducer 24, which translates to about 4 nanoJoules (nJ) of energy per pulse. The energy per pulse may be reduced, for example, by reducing the static capacitance of ultrasonic transducer 24.

The ultrasonic signals 25 can travel through medication 20 along the length of barrel 12 and bounce or reflect off an end 27 of barrel 12 and travel back through medication 20 to plunger head 22. The reflected ultrasonic signals or ultrasonic echo can be received and detected by ultrasonic transducer 24. A velocity V of sound in medication 20 may be a known value and thus a distance D can be calculated, according to the formula: $D=Vt/2$, very accurately where time t is the time it takes for an ultrasonic signal to travel down and back (i.e., 2D) from ultrasonic transducer 24. In other words, distance D can be calculated based on the measured time between when an ultrasonic signal 25 is transmitted by ultrasonic transducer 24 and the ultrasonic echo is detected by ultrasonic transducer 24, and that time is referred to herein as the echo time. As plunger head 22 is moved down barrel 12, distance D will decrease along with the echo time and the volume of medication in barrel 12. And by knowing the radius r of barrel 12 then the volume V of medication 20 dispensed may be calculated based on the change in distance D according to the formula: $V=\pi r^2 D$. A suitable sampling rate of the ultrasonic signals can be selected so that the displacement of plunger head 22 can be accurately tracked regardless of the speed at which plunger 14 may be depressed. For example, in some embodiments, a suitable sampling rate may be about 100 ms, about 80 ms, about 60 ms, about 40 ms, about 20 ms, about 10 ms, or less than about 10 ms. In other embodiments, the sampling rate may be slower to conserve battery life. For example, the sampling rate may be about 1 second.

As shown in FIG. 3, in some embodiments, a porous membrane 29 may be placed within barrel 12 at end 27. Porous membrane 29 may be designed to allow medication 20 to pass through while providing a surface with good reflective properties for the ultrasonic signals 25 to reflect back towards ultrasonic transducer 24. Utilizing porous membrane 29 may improve the accuracy of the echo detection and thereby the distance and volume calculations. It is contemplated that other materials may be used besides a porous membrane. It is also contemplated that the geometry of barrel 12 at end 27 may dictate whether a porous membrane is needed. For example, in some embodiments the geometry of end 27 may be designed to produce the desired reflective properties avoiding the need to employ porous membrane 29.

Microcontroller 26 may be programmed with instructions to control the operation of ultrasonic transducer 24. Microcontroller 26 may be programmed with instructions to calculate data representative of the quantity of medication 20 dispensed. For example, in some embodiments, microcontroller 26 may be programmed to detect and record the echo times of the ultrasonic signals 25. Based on the echo times, microcontroller 26 may calculate distance D and volume V. Microcontroller 26 may also produce an echo time profile of the distance between ultrasonic transducer 24 (i.e., plunger head 22) and end 27. Based on the echo time profile of the distance, microcontroller 26 may be able to identify a first distance $D_1$ or starting position (e.g., before medication 20 is dispensed), which may correspond with barrel 12 being filed and a second distance $D_2$ or ending position (e.g., after medication 20 is dispensed), which may correspond with barrel 12 being empty. Microcontroller 26 may then calculate the change in distance between $D_1$ and $D_2$ and based on this total change in distance may calculate the total volume (i.e., amount or quantity) of medication 20 dispensed. In some embodiments, incremental changes in distance D may be calculated, for example, between each ultrasonic signal 25, as plunger head 22 travels down barrel 12, which may then allow for incremental changes in volume to be calculated. Therefore, the total distance traveled by plunger head 22 and total volume dispensed may be calculated in one or more ways. For example, the total distance traveled and total volume dispensed may be calculated based on the starting position and the ending position or the total distance and total volume may be calculated by totaling the incremental measurements.

Ultrasonic transducer 24 and/or microcontroller 26 may be programmed with instructions to perform various forms of signal conditioning to improve the accuracy by which the echo time of the reflected ultrasonic signals 25 are detected and measured. For example, as plunger head 22 approaches end 27 of barrel 12, when dispensing medication 20, measuring the echo time can become increasingly difficult as the echo time becomes shorter and shorter and are more susceptible to destructive (e.g., multi-path) wave interference. Ordinarily, a front edge of each reflected wave of the ultrasonic signal 25 may be used to measure the echo time. But, as plunger head 22 gets closer to end 27 destructive interference may cause the front edge of the reflected waves to become distorted (e.g., change shape or jump). When the front edge of the reflected wave jumps, this change may not be indicative of actual movement of plunger head 22, but may instead be caused by destructive (e.g., multi-wave) interference. Therefore, if this movement is incorrectly identified as movement of plunger head 22, it can lead to inaccurate measurement of the volume of medication 20 remaining in barrel 12 as well as the volume of medication 20 dispensed.

The front edges of the reflected waves may jump forward (e.g., early or back (e.g., late). When the front edges of the reflected waves jump, the jump will typically be equal to a wavelength of ultrasonic signal 25. In some embodiments, the jump may be equal to an integer multiple of the wavelength (e.g., 2 wavelengths, 3 wavelengths, or more wavelengths). Therefore, in order to improve the accuracy of the echo time measurement, particularly when plunger head 22 approaches end 27, microcontroller 26 may be programmed with instructions to identify and compensate for these jumps. It has been observed that it is about the final 20% of the travel distance of plunger head 22 that is increasingly affected by the destructive interference. Therefore, in some embodiments, microcontroller 26 may be programmed to start executing the instructions that identify and compensate for these jumps when plunger head 22 is down to about the last 20% of the travel distance. In other embodiments, the instructions that identify and compensate for these jumps may always be executing.

In order to identify and compensate for these jumps, microcontroller 26 may be programmed to measure and track the echo time of each wave of ultrasonic signal 25. Microcontroller 26 may then compare the echo time of consecutive echo times to calculate a change in echo times between the consecutive echo times. In some embodiments, microcontroller 26 may calculate a moving average of echo times (e.g., using a low-pass filter) and compare the consecutive measurements of the moving average. And, if the calculated change in distance corresponding to the change in the echo times is above a threshold value, then microcontroller 26 can identify the latest echo time as an error. In some embodiments, the threshold value may be equal to the wavelength of ultrasonic signals 25. When microcontroller 26 identifies an echo time as an error, microcontroller can apply (e.g., subtract or add) a compensation factor, depending on whether the jump was early or late, to the calculated changed in distance to correct the error. For example, when the threshold value is one wavelength, the compensation factor may also be equal to one wavelength. In some embodiments, once the compensation factor is applied, microcontroller 26 may use the corrected change in distance when calculating a total distance traveled by plunger head 22 and total volume of medication dispensed.

When microcontroller 26 compares an echo time to the previous echo time and the change in distance corresponding to the change in echo times is less than the threshold value (e.g., one wavelength of ultrasonic signal 25), microcontroller 26 may be programmed to recognize this change in distance as actual movement of plunger head 22, which microcontroller 26 may use to calculate the total distance traveled by plunger head 22 and total volume of medication dispensed.

Example 1, described below, provides some values and ranges for a functional operation of medication injection device 10 and plunger head 22, according to an exemplary embodiment.

Example 1

According to Example 1, barrel 12 of medication injection device 10 is sized to hold a volume of about 3 ml of medication 20 and configured to allow plunger head 22 to travel a distance D of about 42.5 mm. Microcontroller 26 is programmed to operate at sampling rate of 20 ms. Ultrasonic transducer 24 is constructed to generate the ultrasonic signal 25 at a frequency of about 2.6 MHz. The wavelength of the ultrasonic signals 25 will depend on the frequency and fluid (i.e., medication 20), but for the purposes of Example 1, the medication is assumed to be water. Thus, at a frequency of about 2.6 MHz the ultrasonic signals 25 will have a wavelength of about 0.57 mm. When plunger head 22 is positioned at its starting point, which corresponds to barrel 12 being filled with 3 ml of medication 20 (i.e., water), an echo time for the ultrasonic signals 25 is about 60 microseconds. As plunger 14 is depressed causing plunger head 22 to travel down barrel 12, the echo time decreases. When plunger head 22 reaches the end of barrel 12, the echo time is about 7 microseconds.

Figure 4:
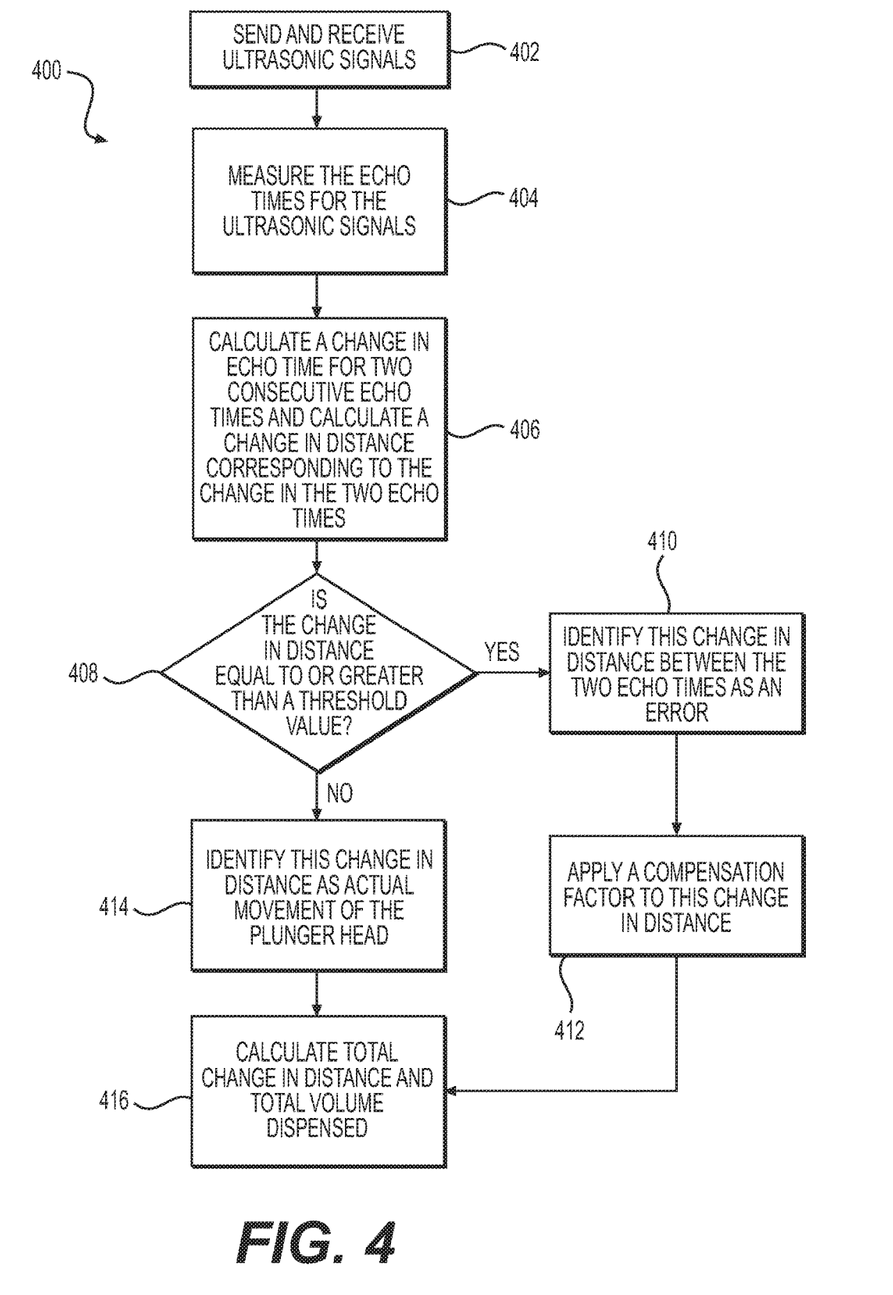
FIG. 4 is a flow chart illustrating a method of error checking and correcting performed by the plunger head of FIG. 2.

FIG. 4 illustrates an exemplary method 400 performed by microcontroller 26 as plunger head 22 travels down barrel 12, which may correspond to Example 1. Exemplary method 400 can identify sampling errors caused by destructive interference and corrects the errors. As plunger head 22 travels down barrel 12, the method may begin by ultrasonic transducer 24 sending and receiving ultrasonic signals 25 (Step 402). At step 404, microcontroller 26 may measure the echo times for the ultrasonic signals 25. In some embodiments, microcontroller 26 may be sending ultrasonic signals at a sampling rate of 20 ms, and after each sampling, microcontroller 26 may be programmed to calculate a change in echo time for two consecutive echo times and calculate a change in distance corresponding to the change in the two echo times (Step 406). If the calculated change in distance between the consecutive echo times is above a threshold value (e.g., a wavelength of the ultrasonic signals 25) (Step 408: Yes), microcontroller 26 may proceed to step 410). At step 410, microcontroller can identify this change in distance between the two echo times as an error. When microcontroller 26 identifies an error, microcontroller 26 can apply (e.g., subtract or add) a compensation factor to the change in distance associated with that sampling, depending on whether the jump was early or late, to correct for the error (Step 412). For some embodiments, the compensation factor may be equal to one wavelength of electrical signals 25. Returning to step 408, if the calculated change in distance between the consecutive echo times is below a threshold value (Step 408: No), microcontroller 26 may proceed to step 414. At step 414, microcontroller 26 may identify this change in distance as actual movement of plunger head 22. At step 416, microcontroller 26 may calculate the total change in distance of plunger head 22 and total dispensed volume of medication 20.

Figure 5:
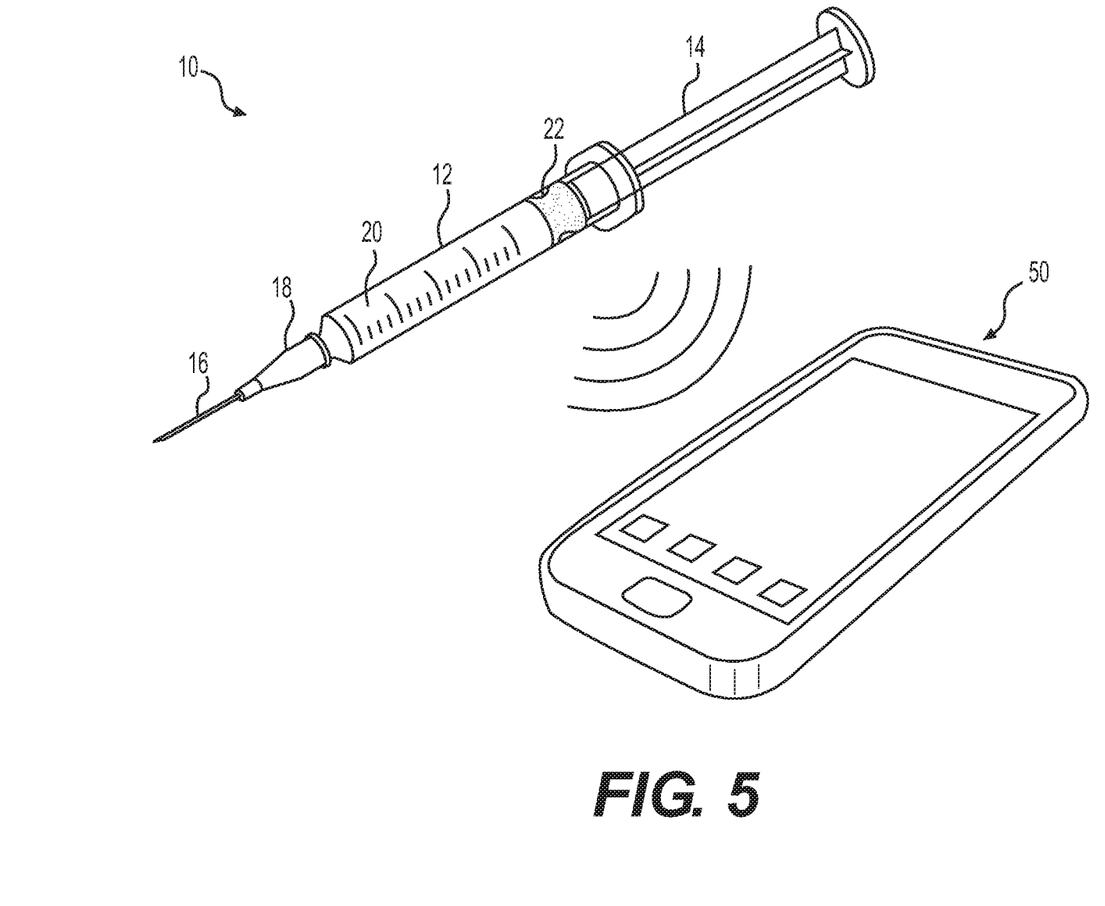
FIG. 5 is a perspective view of the medication injection device of FIG. 1 communicating with a remote device, according to an exemplary embodiment.

Referring now to FIG. 5, plunger head 22 may transmit the amount of medication 20 dispensed along with the time and date it was dispensed to a remote device 50 (e.g., a smart phone, a glucose monitor, an insulin pump, and a computer) via one or more of the wireless communication methods. Plunger head 22 may have a unique identifier so remote device 50 may be able to identify and process the information received properly. Plunger head 22 may transmit this information to remote device 50 immediately or shortly after the medication is administered or plunger head 22 may store the information until remote device 50 is within range. The information may be stored, for example, in memory of microcontroller 26. In some embodiments, plunger head 22 may wait to initiate transmitting of the information until initiated by remote device 50. For example, a user may initiate information retrieval on remote device 50. In some embodiments, remote device 50 may transmit the information to a caregiver (e.g., a doctor) or upload the information to the cloud so it may be saved to the patient's medical history and may be accessed by the caregiver. The ability of a caregiver or a patient to access and review the dose history may improve treatment. For example, the ability of a caregiver to review a diabetic insulin injection history and continuous glucose measurement data may enable the caregiver to adjust the prescribed treatment to improve the therapeutic effect, for example, by better stabilizing the patient's glucose levels.

In some embodiments, microcontroller 26 may be configured to simply detect the echo times of the ultrasonic signals 25 and transmit the echo times to remote device 50 and the remote device may perform all the calculations and signal conditioning operations in order to calculate the volume of medication 20 dispensed.

Plunger head 22 described herein may be utilized for a variety of methods for tracking administering of a medication to a patient delivered by a medication injection device. Various methods of utilizing plunger head 22 will now be explained with reference to FIG. 7. In some embodiments, the methods as described herein may be performed by a caregiver (e.g., a doctor or nurse) in a hospital or other inpatient setting. In some embodiments, the methods as described herein may be performed by a caregiver (e.g., a doctor, nurse, or parent) at home or outside a hospital. In some embodiments, the methods as described herein may be performed by the patient. It is contemplated that the methods described herein may be performed in other settings by other individuals.

Figure 6:
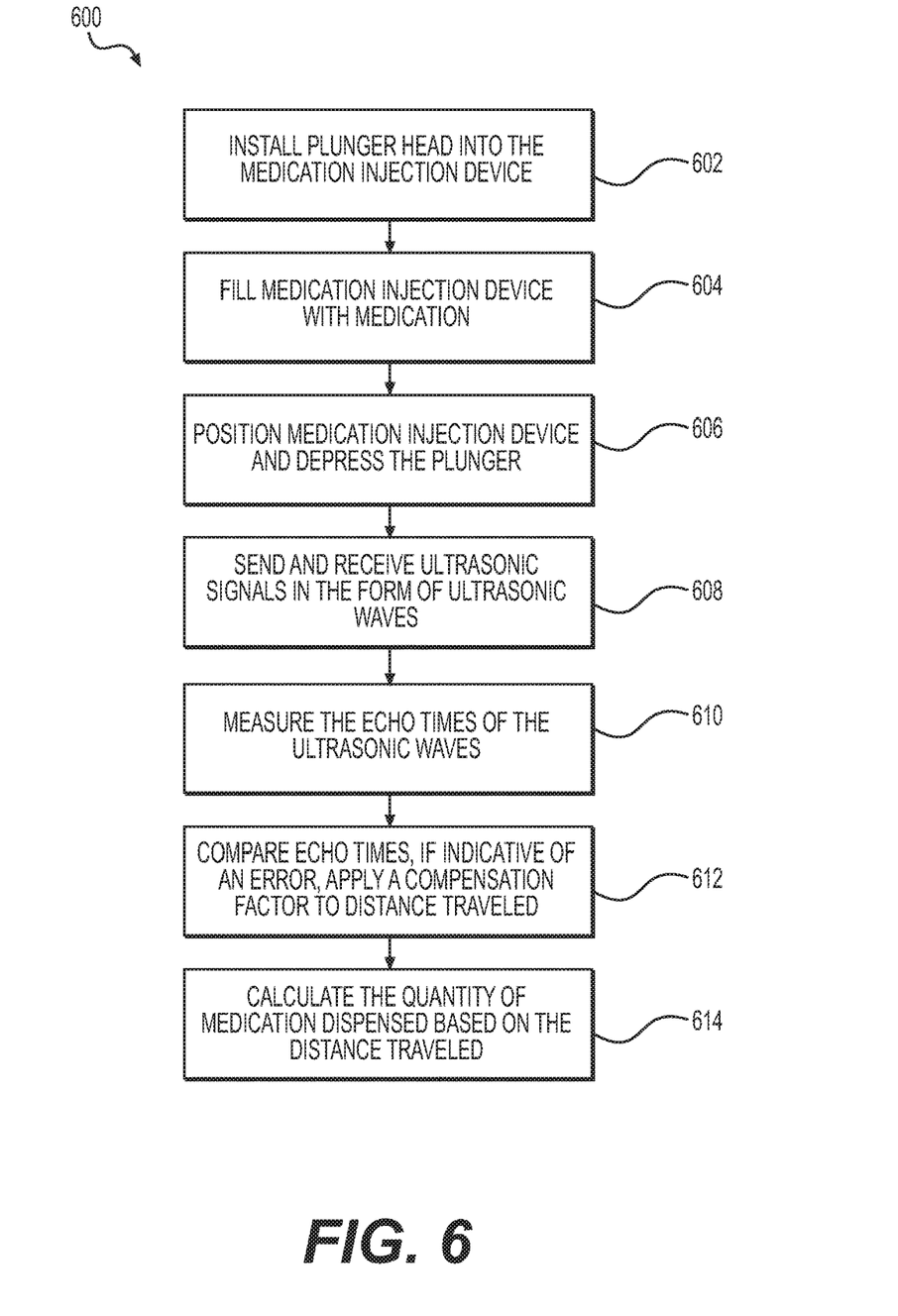
FIG. 6 is a flow chart illustrating a method of tracking administering of medication by a medication injection device, according to an exemplary embodiment.

Plunger head 22 may be utilized for a method 600 of tracking administering of a medication to a patient delivered by a medication injection device, according to an exemplary embodiment, as shown in FIG. 6. Method 600 may incorporate method 400, as described herein, as a subpart of method 600.

In some embodiments, at step 602, method 100 may begin by installing plunger head 22 into barrel 12 of medication injection device 10 (e.g., a disposable syringe). In some embodiments, medication injection device 10 may be supplied with plunger head 22 already installed, thereby eliminating this step.

Next, at step 604, barrel 12 of medication injection device 10 may be filled with medication 20. Barrel 12 may be completely filled or only partially with medication 20. In some embodiments, medication injection device 10 may be supplied prefilled with medication 20, thereby eliminating this step. In some embodiments, plunger head 22 may be configured to "wake up" in response to a force applied during the filling, which may be detected by force sensor 34.

Once filled, at step 606, medication injection device 10 may then be positioned for administration. For example, needle 16 may be inserted into the skin of the patient or into a drug delivery port connected to the patient. Once in position, plunger 14 of medication injection device 10 may be depressed, which forces the medication 20 out the needle 16 as plunger head 22 is forced down barrel 12.

While plunger 14 is being depressed, plunger head 22 may send and receive ultrasonic signals 25 in the form of ultrasonic waves via ultrasonic transducer 24, at step 608. Step 608 may correspond to step 402 of method 400. Plunger head 22 may be configured to send and receive ultrasonic signals 25 the duration of the time, that plunger 14 is being depressed. Plunger head 22 may measure the echo times of the ultrasonic waves, for step 610. Step 610 may correspond to step 404 of method 400.

At step 612, plunger head 22 may compare echo times, and if a change in distance calculated based on a change in the echo times is indicative of an error, then plunger head 22 may apply a compensation factor to the change in distance. Step 612 may correspond to steps 406, 408, 410, and 412 of method 400. At step 614, the quantity of medication 20 dispensed may be calculated based on the calculated distance the plunger head 22 traveled. Step 614 may correspond to step 416 of method 400.

For some embodiments of method 600, the change in distance calculated based on a change in the echo times may be indicative of an error when the change in distance is equal to about one wavelength of the ultrasonic waves. For some embodiments of method 600, at step 612, plunger head 22 may recognize the change in distance as an actual movement of the plunger head when the change in distance calculated based on a change in the echo times is less than one wavelength of the ultrasonic waves.

In some embodiments, method 600 may also include transmitting the quantity of the medication dispensed and the time and date the quantity was dispensed to a remote device. In some embodiments, method 600 may also include uploading the quantity of the medication dispensed and the time and date the quantity was dispensed to the cloud. In some embodiments, method 600 may also include sending the quantity of the medication dispensed and the time and date the quantity was dispensed to a caregiver.

The foregoing description has been presented for purposes of illustration. It is not exhaustive and is not limited to precise forms or embodiments disclosed. Modifications, adaptations, and other applications of the embodiments will be apparent from consideration of the specification and practice of the disclosed embodiments. For example, the described embodiments of plunger head 22 may be adapted for used with a variety of medication injection devices, including for example, syringes, auto-injectors, auto-syringes, injector pens (e.g., insulin pens), or other drug or medication injection devices. The described embodiments of plunger head 22 may be also adapted for use with a variety of other injection or dispensing devices, which may be medical or non-medical related. For example, plunger head 22 may be used in non-medical fluid dispensing applications where the measurement and tracking of the volume of fluid being dispensed is of interest.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Computer programs, program modules, and code based on the written description of this specification, such as those used by the microcontrollers, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

Other embodiments will be apparent from consideration of the specification and practice of the embodiments disclosed herein. It is intended that the specification and examples be considered as example only, with a true scope and spirit of the disclosed embodiments being indicated by the following claims.

The invention claimed is:

1. A plunger head, comprising:
   an elastomer housing configured to fit within a barrel of a medication injection device;
   an ultrasonic transducer configured to send and receive ultrasonic signals as ultrasonic waves;
   an antenna;
   a microcontroller electrically coupled to the ultrasonic transducer and the antenna; and
   a power source electrically coupled to the microcontroller and the ultrasonic transducer and configured to power the microcontroller and the ultrasonic transducer;
   wherein the ultrasonic transducer, the antenna, the microcontroller, and the power source are at least partially encapsulated in the elastomer housing;
   wherein the microcontroller is programmed with instructions that when executed by the microcontroller cause the plunger head to perform operations including:
   measuring echo times of the ultrasonic waves;

comparing consecutive echo times of the ultrasonic waves to determine a change in distance travelled by the plunger head;

assessing whether the change in distance is deemed to be indicative of an error;

applying a compensation factor to the change in distance when the change in distance is deemed to be indicative of the error; and calculating a volume of medication dispensed from the barrel based on the change in distance of the plunger head, as compensated by the compensation factor when the change in distance is deemed to be indicative of the error.

2. The plunger head of claim 1, wherein assessing whether the change in distance is deemed to be indicative of the error comprises:

identifying when the change in distance is greater than or equal to about one wavelength of the ultrasonic waves.

3. The plunger head of claim 2, wherein the compensation factor is equal to about one wavelength of the ultrasonic waves.

4. The plunger head of claim 1, wherein the microcontroller is programmed with further instructions that when executed by the microcontroller cause the plunder head to perform additional operations comprising:

determining that the change in distance is not indicative of the error when the change in distance is less than one wavelength of the ultrasonic waves.

5. The plunger head of claim 1, wherein the ultrasonic signals have a frequency between about 2 Mhz and about 3 Mhz.

6. The plunger head of claim 1, wherein the microcontroller is programmed with further instructions that when executed by the microcontroller cause the plunger head to perform additional operations comprising:

starting to assess whether the change in distance is deemed to be indicative of the error only after the plunger head reaches a last 20% of a total available travel distance of the plunger head within the barrel.

7. The plunger head of claim 1, wherein the microcontroller is programmed with further instructions that when executed by the microcontroller cause the plunger head to perform additional operations comprising:

transmitting data indicative of the volume of medication dispensed from the barrel to a remote device via the antenna.

8. The plunger head of claim 7, wherein the microcontroller is programmed with further instructions that when executed by the microcontroller cause the plunger head to perform additional operations comprising:

registering a date and time the volume of medication is dispensed; and transmitting the date and time to the remote device along with the data indicative of the volume of medication dispensed.

9. The plunger head of claim 1, further comprising a temperature sensor configured to measure a temperature of the volume of medication, wherein the microcontroller is programmed with further instructions that when executed by the microcontroller cause the plunger head to perform additional operations comprising:

compensating for changes in the temperature of the volume of medication when calculating the volume of medication dispensed.

10. The plunger head of claim 1, wherein the medication injection device is at least one of a disposable syringe, an auto-injector, or insulin pen.

* * * * *